United States Patent [19]

McQuilkin et al.

[11] Patent Number: 4,888,000
[45] Date of Patent: Dec. 19, 1989

[54] APPARATUS FOR THE INSERTION OF CATHETERS

[75] Inventors: Peter H. McQuilkin; William T. Lawrence, both of Nottingham, England

[73] Assignee: Femcare Limited, Nottingham, England

[21] Appl. No.: 202,055

[22] Filed: Jun. 3, 1988

[30] Foreign Application Priority Data

Jun. 4, 1987 [GB] United Kingdom ................ 8713093

[51] Int. Cl.$^4$ ............................................. A61M 5/00
[52] U.S. Cl. .................................... 604/164; 604/160; 604/168
[58] Field of Search ........ 604/164, 160, 168, 272–274, 604/170

[56] References Cited

U.S. PATENT DOCUMENTS

| | | | |
|---|---|---|---|
| 4,077,412 | 3/1978 | Moosun | 604/164 |
| 4,306,562 | 12/1981 | Osborne | 604/164 |
| 4,636,199 | 1/1987 | Victor | 604/164 |

Primary Examiner—Stephen C. Pellegrino
Attorney, Agent, or Firm—Salter & Michaelson

[57] ABSTRACT

A supra pubic catheter is inserted via a cannula which is positioned using a trocar, the trocar being withdrawn to leave the cannula in position through the wall of the bladder allowing passage of the supra pubic catheter, the canula being provided with means for subsequent removal from the catheter.

1 Claim, 2 Drawing Sheets

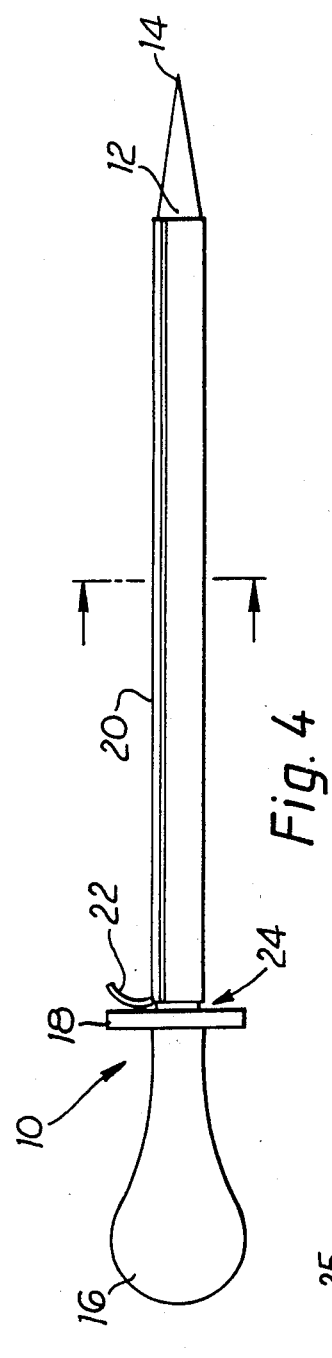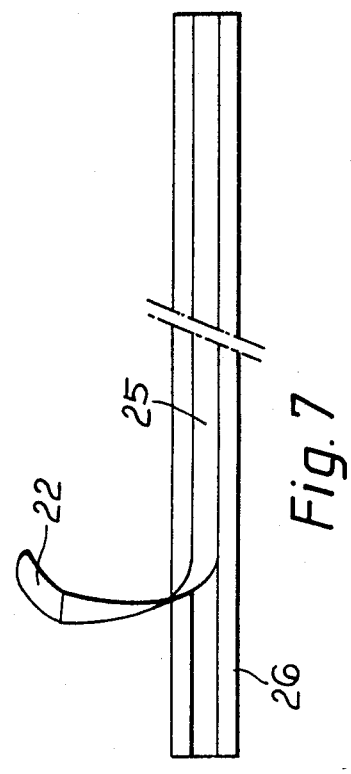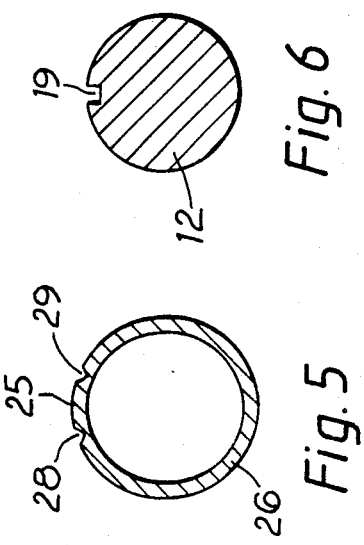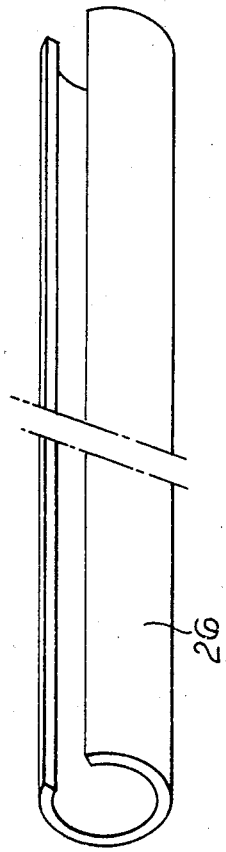

APPARATUS FOR THE INSERTION OF CATHETERS

The present invention relates to apparatus for the insertion of catheters, and more particularly to a cannula and trocar for the insertion of a supra pubic catheter.

Supra pubic catheters are used for the drainage of urine in patients and are inserted, according to one known method, by pushing a surgical instrument through the wall of the bladder and through the abdominal wall by a suitable incision attaching the catheter to the end of the instrument by surgical stitches and drawing the intrument backwards until the catheter is visible the surgical stitches then being removed and the catheter then being drawn back into the bladder to accomplish the required drainage process. This procedure is firstly very time consuming and secondly it is usually extremely uncomfortable for the patient. The surgical instrument, being expensive also requires sterilisation after each operation.

It is an object of the present invention to provide apparatus for the insertion of a supra pubic catheter the apparatus comprising a disposable trocar inside a disposable cannula the cannula being provided with means for allowing removal of the cannula from the supra pubic catheter after fitting the supra pubic catheter into a patient via the cannula in which the trocar is provided with a full length longitudinal channel which allows easy passage of a liquid between the trocar and cannula in which the cannular is provided with at least one reduced wall section to provide easy removal in which the cannula is provided with a grasping tab connected to the material between the reduced wall sections to provide a purchase for easy removal, and in which the trocar is provided with a shoulder abutting one end of the cannula to provide support for the cannula during insertion.

Embodiments of the present invention will now be described, by way of example with reference to the accompanying drawings, in which:

FIG. 1 diagrammatically illustrates the insertion of the apparatus according to the present invention for the subsequent insertion of a supra pubic catheter;

FIG. 4 shows a possible design of disposable cannula and trocar used in the insertion method of FIGS. 1 to 3;

FIG. 5 shows a cross-section through the cannula of FIG. 4;

FIG. 6 shows a cross-section through the trocar of FIG. 4;

FIG. 7 shows the cannula of FIGS. 4 and 5 with part of the removable section lifted; and FIG. 8 shows a perspective view of the cannula with the removable section having been removed.

Figure 1:
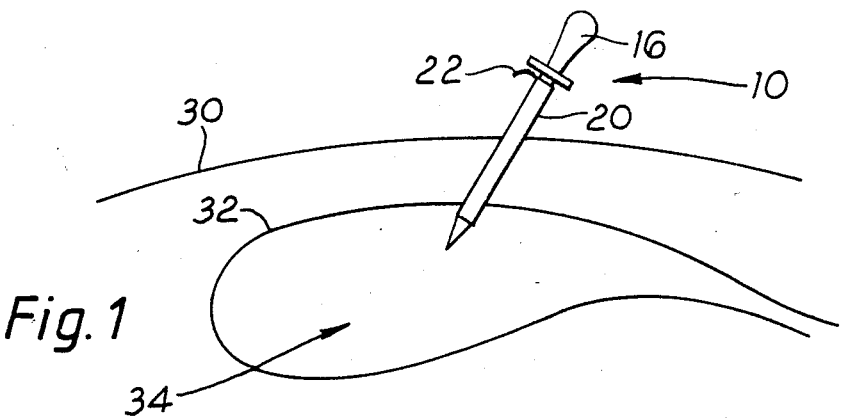
Figure 2:
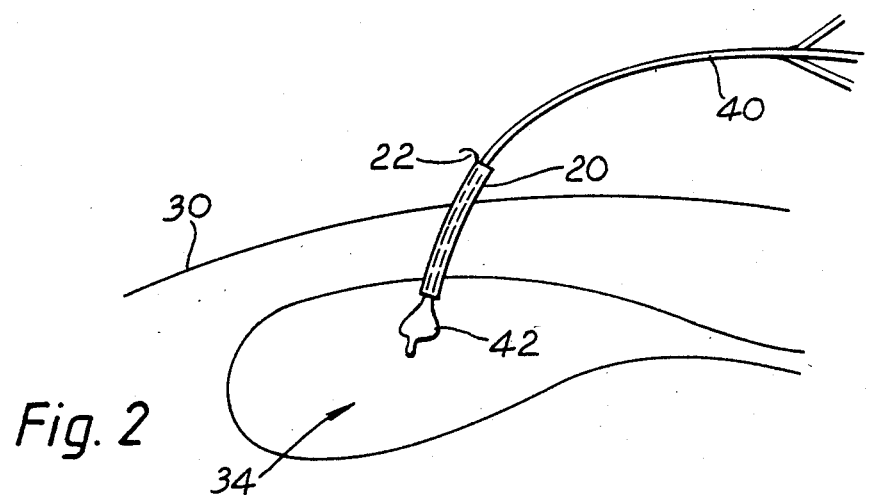
FIG. 2 shows a second stage in the insertion process.
Figure 3:
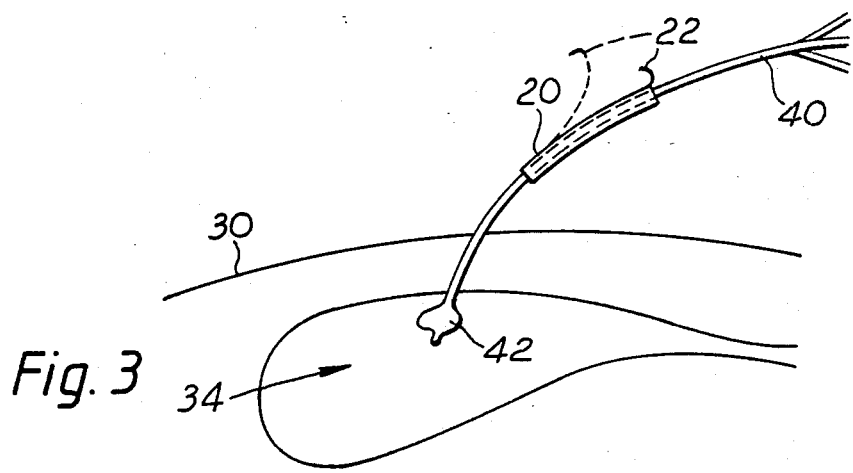
FIG. 3 shows a third stage showing the removal of the cannula of FIGS. 1 and 2.

With reference now to FIGS. 1 to 3 the apparatus according to the present invention comprises a trocar 10 and cannula 20 forming a unit by the insertion of the trocar into the cannula. Preferably the trocar and cannula will be manufactured from a hygienic plastics material or materials and will be pre-assembled as shown in FIG. 4. They will be therefore relatively cheap and may therefore both be disposed of after one operation.

The trocar (with attached cannula) is pushed through the skin 30 of the patient (after an initial small incision) and through the wall 32 of the bladder 34, the bladder 34 having been previously filled with for example a saline solution to fill the bladder and provide resistance to the entry of the trocar and cannula assembly.

When the trocar and cannula assembly enters the bladder this is detected by the seepage of the saline solution (as described hereinafter) and the trocar is then withdrawn from inside the cannula leaving the cannula as an open channel into the bladder. The supra pubic catheter 40 is then inserted into the bladder via the cannula 20 and in known manner the end 42 of the catheter is inflated to retain the catheter inside the bladder. The catheter is then in known manner used to drain fluid from the bladder.

The insertion of the catheter leaves the cannula still present and following insertion and inflation it is desirable to remove the cannula. This is achieved by pulling the cannula from the body of the patient as shown in FIG. 3 and then removing the longitudinal section by grasping the tab 22 as described hereinafter. The end of the catheter is then able to be covered for example by a piece of plaster (not shown) in known manner to hygienically seal the hole made by the cannula and trocar.

With reference now to FIGS. 4 to 7 the trocar comprises in known manner a rigid or semi-rigid rod 12 with a sharpened end 14 which may be pointed or chisel-shaped etc. A handle portion 16 is provided for gripping the trocar and a collar 18 is provided for supporting the end 24 of cannula 20 against movement by the forces existing during insertion of the trocar into the body of the patient.

The cannula comprises a hollow tube 26 (see FIG. 5) preferably of essentially of circular cross-section. Two longitudinal reduced wall thickness frangible sections 28, 29 are provided which are thereby weaker than the rest of the cannula and these define a longitudinal removable section 25, to which is attached the grasping tab 22.

With reference to FIG. 6 the trocar rod 12 is provided with a full length longitudinal channel 19. When the trocar pierces the bladder wall 32 the saline fluid within the bladder escapes up the channel 19 and seeps out at the collar end 18 of the trocar 10. This is readily observable by the surgeon and provides a sure indication that the trocar and cannula assembly is safely within the bladder.

With reference to FIGS. 3 and 7 once the supra pubic catheter has been correctly inserted the cannula can then be withdrawn leaving the catheter in position and it can be readily removed from the catheter 40 as shown in FIG. 8 by tearing off the removable section 25 leaving the catheter free of any contaminated material.

We claim:

1. An apparatus for inserting a supra pubic catheter in a patient comprising a substantially rigid, disposable, tubular canula and a substantially rigid disposable trocar slidably received in said canula, said trocar having distal and proximal ends and having a shoulder adjacent the proximal end thereof, said trocar having a longitudinal channel formed therein which extends along substantially the entire length thereof to permit the passage of a fluid between said trocar and said canula, said trocar being removable from said canula for installing a supra pubic catheter in said canula, said canula having distal and proximal ends and being sufficiently rigid to permit the advancement of the distal end thereof through the stomach wall of a patient by engaging the proximal end of said canula with said shoulder, said canula including a pair of closely spaced longitudinally extending frangible sections of reduced wall thickness which define a longitudinally extending removable section therebetween, said removable section being removable from the remaining portion of said canula to form a longitudinally extending open slot in said canula which extends along the entire length thereof, said canula being removable from a supra pubic catheter received therein by removing said removable section from the remaining portion of said canula and passing said catheter through said slot.

* * * * *